May 7, 1940. W. M. McILVAINE Plant Pat. 388
APPLE TREE
Filed Sept. 8, 1939
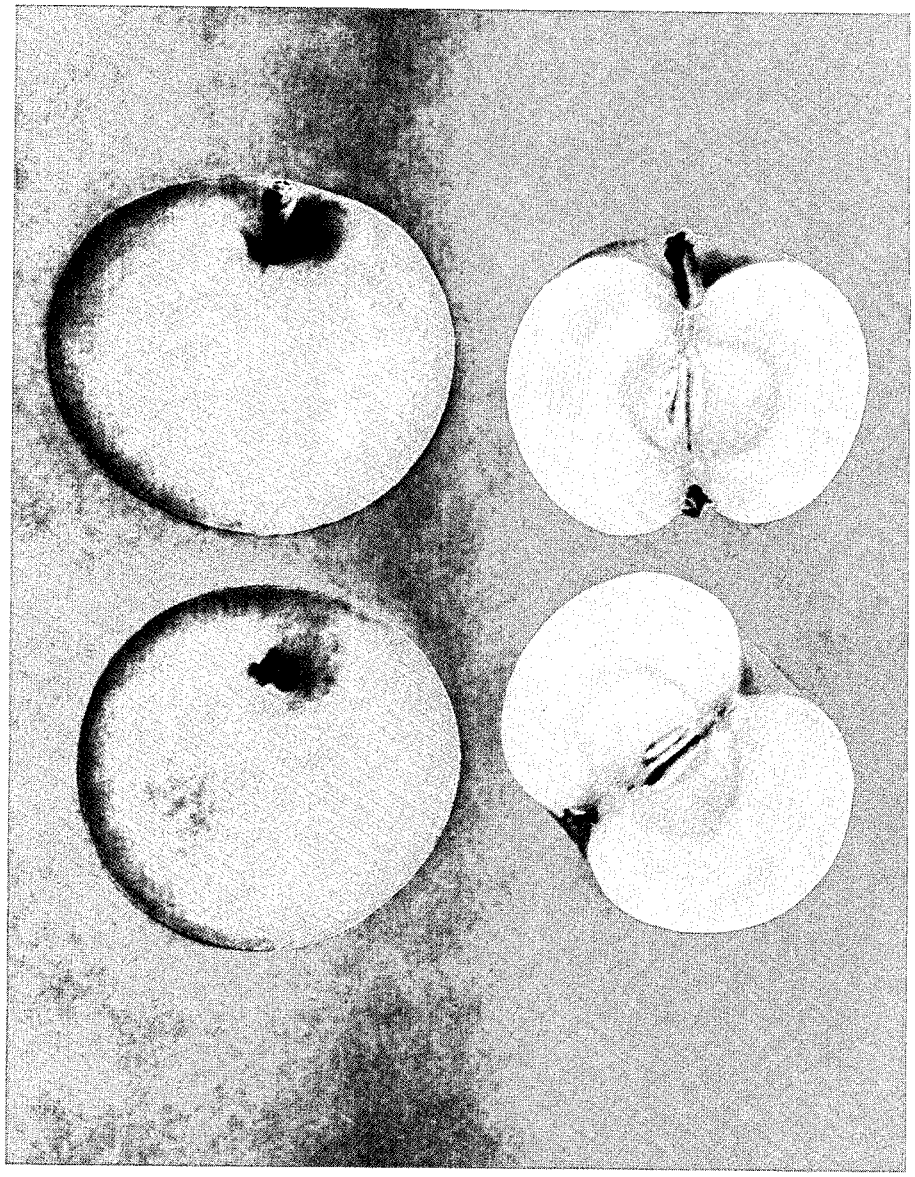
INVENTOR
W. M. McIlvaine
by J. R. McIlvaine &
V. M. Barnett
Administrators of the estate
of W. M. McIlvaine, deceased
By Robb & Robb
Attorneys Patented May 7, 1940

Plant Pat. 388

UNITED STATES PATENT OFFICE

388

APPLE TREE

Wrixhem M. McIlvaine, deceased, late of Magnolia, Del., by J. Ralph McIlvaine, Magnolia, Del., and Vernon M. Barnett, Chestertown, Md., administrators, assignors to Bountiful Ridge Nurseries, Princess Anne, Md.

Application September 8, 1939, Serial No. 294,030

1 Claim. (Cl. 47—62)

The present discovery relates to a new and distinct variety of apple tree, originating as a seedling and having as its primary feature of novelty the early ripening characteristic of its fruit.

It is generally supposed, according to records, that the Yellow Transparent variety of apple is the earliest ripening cooking apple now on the market, for which reason, the new variety may be best compared with it when grown under comparable conditions. It is notable that this new variety ripens from ten days to two weeks earlier than the Yellow Transparent, usually coming to full maturity and passing several days before it is possible to ship the Yellow Transparent.

In addition to this valuable ripening characteristic of the new variety, it is distinguishable by virtue of the fact that it is an annual bearer, whereas the Yellow Transparent is more or less a biennial bearer; that it is larger in size than the other early apples; possesses a distinct and clear green color; will carry long distances in shipping; has splendid cooking qualities, and when fairly ripe has a fair eating quality.

The new variety is also distinct in its shape from any other apple which will even approach its season.

Referring more particularly to its size, it may be stated that it seldom picks less than 2¼ inch and nearly always 2½ inch grade. By way of comparison, the Yellow Transparent seldom picks larger than 2 inches during the early part of the picking season and is generally packed in the 1¾ and 2 inch sizes.

This new variety has been asexually reproduced and its characteristics found to be fixed.

The following is a detail description of the new variety, the color terminology being in accord with the general dictionary terms except where otherwise indicated:

Specimens described were grown at Magnolia, Delaware.

Dates first and last picking: June 21–June 27.

Tree: Medium size; vigorous; spreading; low; vase-formed; slow growing; hardy; very productive; regular bearing.

Trunk: Medium stocky; smooth.

Tree:

*Branches.*—Thick; smooth; branching; Brown-Gray.

*Lenticels.*—Medium number; small.

*Leaves.*—Length—4″; width—3″ up to 3½ x 5″. Large; wide; long; oval; abruptly pointed; thick; Dark Green; rugose. Margin—crenate. Petiole: length—¾″ (½ to 1″); medium length; thick.

*Flowers.*—Date of first—April 22. Full bloom—April 26. Medium early; large size; White; blossom similar to Yellow Transparent, tinge of pink on petals.

Fruit: Maturity when described—eating hard under ripe date June 20, 1939.

*Size.*—Variable; axial diameter—2″; transverse—2½″.

*Form.*—Irregular; oblate; angular. Cavity—symmetrical; rounded, flaring toward apex; undulate. Depth—¼″; breadth—⅞″; markings occasional russet rays or suture. Basin—symmetrical, rounded; flaring; narrow; furrowed; undulate; glabrous. Depth — ⅛″; breadth — ⅝″. Markings—none.

*Stem.*—Clubbed; stout; pubescent. Length—⅜″ (⅛ to ¾″); breadth—$\frac{3}{32}$ to ⅛″. Markings—none.

*Calyx.*—Closed; persistent; broadly lanceolate; acute; ⅜″ long; imbricate at base; ascending; converged from base toward center; connivent. Outer surface and inner surface—pubescent.

*Eye.*—Medium size.

*Skin.*—Thick; tough; smooth; glossy; waxed. Dots conspicuous, many, large, even, oblong, aerolar. Color of dots—White. Distribution of dots over apple—more at basin end. Ground color—Light Green, Plate 19K4 (Maerz & Paul). Color markings—none. Bloom—abundant. Scarfskin—wanting. General color effect—uniform Light Green.

*Flesh.*—Juicy. Color of flesh—White with greenish tinge. Texture—hard, tender, granular, coarse, crisp. Flavor—subacid. Aroma—wanting. Quality—good.

*Core.*—Median. Bundle area (longitudinal section)—medium size, orbicular; symmetrical at base; in bundle opposite with cell. Halves of area—unequal. Bundles—Green, inconspicuous in one whorl. Alternate bundle—reaches calyx tube above stamens. Core lines—clasping. In cross section—distinct. Carpellary area—distinct, small. Calyx tube—pubescent, cone-shaped. Entire depth—⅜''. Styles—present; united toward base; pubescent. Stamens—in one distinct whorl; median. Auxiliary cavity—wanting. Seed cells—abaxile; open. Cell walls — thick, tough. Length — ⅞''. Breadth—⅜''. Longitudinal section—narrowly ovate; emarginate; obtuse at apex. Surface—fissured; cross section—narrow.

*Seeds.*—Number perfect—4 to 5; imperfect—1. Number in one cell—1–2; length—⅜''. Breadth—$\frac{3}{16}$''. Form—acuminate.

*Use.*—Market; culinary.

*Keeping quality.*—Good. Number of days in ordinary storage—10 days.

*Resistance to.*—Insects—good. Diseases—good.

General notes: Similar to Williams in shape of tree. Branches are similar in color to Yellow Transparent but more grayish. Blossom is similar to Yellow Transparent except for more pink in this bloom.

On June 20, fruits of Yellow Transparent were practically all below 2'' in size, compared with 80% of 2¼'' to 2½'' and some 2½'' plus on the trees of this new fruit.

What is claimed as novel is:

A new and distinct variety of apple three characterized as to novelty by its early ripening and annual bearing habits; the large size, unusual shape, and clear distinct green color of its fruit; the splendid cooking and eating qualities, and the excellent shipping quality of said fruit.

J. RALPH McILVAINE,
VERNON M. BARNETT,
*Administrators of the Estate of Wrixhem M. McIlvaine, Deceased.*